(12) United States Patent
Feinstein (10) Patent No.: US 10,981,003 B1
(45) Date of Patent: Apr. 20, 2021

(54) SYSTEM AND METHOD EMPLOYING INTERFERENTIAL ELECTRICAL STIMULATION FOLLOWING SHOULDER SURGERY

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 17/108,210

(22) Filed: Dec. 1, 2020

(51) Int. Cl.
| | | |
|---|---|---|
| *A61N 1/36* | (2006.01) | |
| *A61N 1/32* | (2006.01) | |
| *A61N 1/04* | (2006.01) | |
| *A61B 90/00* | (2016.01) | |

(52) U.S. Cl.
CPC .............. *A61N 1/323* (2013.01); *A61B 90/39* (2016.02); *A61N 1/0456* (2013.01); *A61N 1/36031* (2017.08); *A61N 1/36034* (2017.08); *A61B 2090/395* (2016.02); *A61B 2090/3933* (2016.02); *A61B 2090/3966* (2016.02)

(58) Field of Classification Search
CPC ................ A61N 1/323; A61N 1/36031; A61N 1/36034; A61N 1/0456; A61B 90/39; A61B 2090/395; A61B 2090/3933; A61B 2090/3966
See application file for complete search history.

(56) References Cited

U.S. PATENT DOCUMENTS

| | | | |
|---|---|---|---|
| 6,972,022 B1* | 12/2005 | Griffin .................. | A61B 90/39 604/112 |
| 9,067,080 B2 | 6/2015 | Einy | |
| 10,456,573 B1* | 10/2019 | Feinstein ............. | A61N 1/0456 |
| 10,682,512 B1 | 6/2020 | Feinstein | |
| 2008/0097564 A1* | 4/2008 | Lathrop ................. | A61N 1/321 607/115 |
| 2008/0208287 A1* | 8/2008 | Palermo ............... | A61N 1/0526 607/48 |
| 2011/0150924 A1* | 6/2011 | Della Rocca .......... | A61N 1/306 424/204.1 |
| 2016/0030737 A1 | 2/2016 | Gerasimenko et al. | |

(Continued)

OTHER PUBLICATIONS

Gregg J. Jarit et al., "The Effects of Home Interferential Therapy on Post-Operative Pain, Edema, and Range of Motion of the Knee", Clinical Journal of Sports Medicine, vol. 13, No. 1, 2003.

*Primary Examiner* — Amanda K Hulbert
*Assistant Examiner* — Natasha Patel
(74) *Attorney, Agent, or Firm* — Forge IP, PLLC (57) ABSTRACT

An interferential current therapy kit for treatment of a patient following an orthopedic shoulder surgery includes, within a container for facilitating the distribution and transport of the kit, a first plurality of electrodes, a second plurality of electrodes and an interferential current therapy control unit. The interferential current therapy control unit is configured to supply interferential current electrical impulses, via the electrodes, so as to give rise to at least one first beat impulse acting on the suprascapular nerve of the patient and so as to give rise to the at least one second beat impulse acting on at least one of an axillary nerve and a supraclavicular nerve of the patient.

21 Claims, 6 Drawing Sheets

(56) References Cited

U.S. PATENT DOCUMENTS

2016/0317383 A1* 11/2016 Stanfield .............. A61B 5/6804
2016/0325071 A1    11/2016 Shambroom et al.
2017/0319273 A1* 11/2017 Wu ................... A61M 25/0141
2020/0188660 A1*  6/2020 Franke ................. A61B 18/14

* cited by examiner

FIG. 3
(ANTERIOR VIEW)

FIG. 4

(POSTERIOR VIEW)

SYSTEM AND METHOD EMPLOYING INTERFERENTIAL ELECTRICAL STIMULATION FOLLOWING SHOULDER SURGERY

FIELD OF THE INVENTION

The invention relates to a system and method employing the use of an electrical stimulator, such as an Interferential Current (IFC) device, or other type of deep penetration electrical stimulation that is non-invasive and external (i.e., transcutaneous), for treatment following orthopedic surgeries. More specifically, the invention relates to a treatment system and method of the type described for pain management and/or reducing edema following shoulder surgeries, such as shoulder arthroscopies, as well as partial and full shoulder arthroplasties.

BACKGROUND OF THE INVENTION

The theory of electrical stimulation therapy for pain control has been studied at significant length since it was initially theorized. Historically, the use of electrical properties to control pain dates back to 46 AD when torpedo fish were used to treat headache and gout. The theory behind the effectiveness of the use of electrical stimulation for pain has been described as the gate theory of pain modulation, which describes how pain stimulation can be blocked from reaching the brain by other signals. This theory has provided the bases for pain management with electrical stimulation using different modalities. In the 1950s, the use of interferential current therapy (IFC) was developed to provide dual current therapy to provide deeper tissue penetration to allow for improved pain relief.

In the field of orthopedic surgery, several studies have compared the use of electrical stimulation therapy for patient pain relief with differing results. Two systematic reviews were done comparing use of transcutaneous electrical nerve stimulation (TENS) as a possible adjunct after total knee arthroplasty (TKA). Both studies found significant improvement of pain scales and active knee range of motion.

More specifically, IFC therapy has also been compared to both TENS and placebo for pain relief. When compared to TENS for back pain, there are conflicting results. Some studies indicate overall pain improvement but no difference between modalities. Another study found IFC to be more effective in treating chronic low back pain due to deeper tissue penetration. The author of this patent application is an Orthopedic Surgeon, and has compared TENS unit treatment to IFC treatment in clinical practice with findings of IFC use to be far more effective than TENS for treatment of muscular and neurogenic pain.

One study out of Kerlan-Jobe Orthopedic clinic in 2001 compared IFC therapy to placebo for post-operative pain, edema and range of motion after ACL, meniscectomy or knee chondroplasty. In this randomized, double-blind, placebo controlled prospective study, patients were treated post-operative with IFC therapy providing therapeutic or placebo electrical stimulation. In the study, all IFC subjects reported significantly less pain and greater range of motion for all reviewed time points.

The techniques of the Kerlan-Jobe study were improved upon, as described in U.S. Pat. No. 10,682,512, by providing for a system and method employing IFC therapy that may be used by patients following orthopedic surgeries, for example, following knee arthroplasty surgery. The invention disclosed therein provides for improved patient outcomes, which result in shorter hospital stay, reduced use of opioid medication and decreased need for manipulation under anesthesia.

The present invention builds upon the techniques described in U.S. Pat. No. 10,682,512, but is specifically targeted at providing improved outcomes following shoulder surgeries, including shoulder arthroscopies, as well as partial and full shoulder arthroplasties.

SUMMARY OF THE INVENTION

Accordingly, one object of the present invention is to provide a system and method that results in reduced pain, increased range of motion and/or reduced edema following shoulder surgery.

Such a system and method allows for the present invention to be safely implemented and used in the immediate post-operative care timeframe (whether inpatient or outpatient) upon completion of the surgical procedure, by allowing the surgeon, the surgeon's supporting personnel, and the patient's care team (such as nurses, surgical techs, physicians assistants, physical therapists, etc.) to safely and consistently apply and use the invention.

It is another object of the present invention to provide such a system and method that may be safely employed by the patients by themselves or together with healthcare personnel after having been released from the hospital and/or health care facility.

It is also an object of the present invention to provide such a system and method that facilitates use by the patient and/or the surgeon and the patient's health care team, and that minimizes the chances of accidental or inadvertent misuse and/or harm to the patient.

At least some of these, and other, objects may be achieved in accordance with the invention by provision of a kit that may be provided to a patient, the surgeon and patient's healthcare team, the operating room, the hospital and/or the hospital supply chain/vendors, with such a kit incorporating all items needed to employ the inventive system and method to the patient.

More specifically, in accordance with a first aspect of the present invention, an interferential current therapy kit for treatment of a patient following an orthopedic shoulder surgery includes, within a container for facilitating the distribution and transport of the kit, a first plurality of electrodes, a second plurality of electrodes and an interferential current therapy control unit. The first plurality of electrodes is configured to be disposed on an epidermis of the patient and arranged to supply transcutaneous electrical impulses to a suprascapular nerve of the patient when supplied with power, wherein the first plurality of electrodes comprises at least two electrodes adapted to supply transcutaneous electrical impulses at two different frequencies, the transcutaneous electrical impulses provided at two different frequencies adapted to give rise to at least one first beat impulse having an interference frequency. The second plurality of electrodes is configured to be disposed on the epidermis of the patient and arranged to supply transcutaneous electrical impulses to at least one of an axillary nerve and a supraclavicular nerve of the patient when supplied with power, wherein the second plurality of electrodes comprises at least two electrodes adapted to supply transcutaneous electrical impulses at two different frequencies, the transcutaneous electrical impulses provided at two different frequencies adapted to give rise to at least one second beat impulse having an interference frequency. The interferential current therapy control unit comprises a stimulation power supply in electrical communication with the first plurality of electrodes and the second plurality of electrodes, the interferential current therapy control unit configured to supply interferential current electrical impulses so as to give rise to the at least one first beat impulse acting on the suprascapular nerve of the patient and so as to give rise to the at least one second beat impulse acting on at least one of the axillary nerve and the supraclavicular nerve of the patient.

In some embodiments, the interferential current therapy kit further includes an electrode placement aid adapted to assist the patient with placement of the first and second plurality of electrodes with respect to a site of the previous orthopedic surgery, thereby increasing a likelihood of efficacious placement of the plurality of electrodes.

In some embodiments, the electrode placement aid comprises a marking instrument. In certain of these embodiments, the marking instrument comprises an ink marker.

In some embodiments, the electrode placement aid comprises a template. In certain of these embodiments, the template comprises a drape that includes at least one of openings and markings showing a relative intended placement of the plurality of electrodes with respect to anatomical structure.

In some embodiments, the electrode placement aid comprises a measuring device. In certain of these embodiments, the measuring device comprises at least one of a ruler and a tape measure.

In some embodiments, the electrode placement aid comprises an x-ray marker. In certain of these embodiments, the x-ray marker comprises at least one of the following: radiology tape with metal beads, radiology tape with a central strip of radiopaque marker and other radiology devices which are radiopaque, but are not metallic in nature.

In some embodiments, the electrode placement aid comprises an imaging device adapted to assist with electrode placement. In certain of these embodiments, the imaging device is adapted to interface with a mobile phone or tablet.

In some embodiments, the electrode placement aid is adapted to interface with markings created on a body of the patient.

In some embodiments, the control unit further comprises at least one sensor adapted to provide sensor feedback indicative of a patient parameter derived from the patient.

In some embodiments, the interferential current therapy kit further includes a plurality of wire leads adapted to connect the control unit with the plurality of electrodes.

In some embodiments, the first plurality of electrodes comprises a first pair of electrodes configured to be disposed on an anterior of the patient and arranged to supply transcutaneous electrical impulses to the suprascapular nerve of the patient when supplied with power and a second pair of electrodes configured to be disposed on a posterior of the patient and arranged to supply transcutaneous electrical impulses to the suprascapular nerve of the patient when supplied with power.

In some embodiments, the second plurality of electrodes comprises a first pair of electrodes configured to be disposed on an anterior of the patient and arranged to supply transcutaneous electrical impulses to at least one of the axillary nerve and the supraclavicular nerve of the patient when supplied with power and a second pair of electrodes configured to be disposed on a posterior of the patient and arranged to supply transcutaneous electrical impulses to at least one of the axillary nerve and the supraclavicular nerve of the patient when supplied with power.

In accordance with another aspect of the invention, an interferential current therapy kit for treatment of a patient following an orthopedic shoulder surgery, includes a first plurality of electrodes, a second plurality of electrodes, an interferential current therapy control unit and an electrode placement aid. The first plurality of electrodes is configured to be disposed on an epidermis of the patient and arranged to supply transcutaneous electrical impulses to a suprascapular nerve of the patient when supplied with power, wherein the first plurality of electrodes comprises at least two electrodes adapted to supply transcutaneous electrical impulses at two different frequencies, the transcutaneous electrical impulses provided at two different frequencies adapted to give rise to at least one first beat impulse having an interference frequency. The first plurality of electrodes comprises a first pair of electrodes configured to be disposed on an anterior of the patient and arranged to supply transcutaneous electrical impulses to the suprascapular nerve of the patient when supplied with power and a second pair of electrodes configured to be disposed on a posterior of the patient and arranged to supply transcutaneous electrical impulses to the suprascapular nerve of the patient when supplied with power. The second plurality of electrodes is configured to be disposed on the epidermis of the patient and arranged to supply transcutaneous electrical impulses to at least one of an axillary nerve and a supraclavicular nerve of the patient when supplied with power, wherein the second plurality of electrodes comprises at least two electrodes adapted to supply transcutaneous electrical impulses at two different frequencies, the transcutaneous electrical impulses provided at two different frequencies adapted to give rise to at least one second beat impulse having an interference frequency. The second plurality of electrodes comprises a third pair of electrodes configured to be disposed on an anterior of the patient and arranged to supply transcutaneous electrical impulses to at least one of the axillary nerve and the supraclavicular nerve of the patient when supplied with power and a fourth pair of electrodes configured to be disposed on a posterior of the patient and arranged to supply transcutaneous electrical impulses to at least one of the axillary nerve and the supraclavicular nerve of the patient when supplied with power. The interferential current therapy control unit comprises a stimulation power supply in electrical communication with the first plurality of electrodes and the second plurality of electrodes, the interferential current therapy control unit configured to supply interferential current electrical impulses so as to give rise to the at least one first beat impulse acting on the suprascapular nerve of the patient and so as to give rise to the at least one second beat impulse acting on at least one of the axillary nerve and the supraclavicular nerve of the patient. The electrode placement aid is adapted to assist the patient with placement of the first and second plurality of electrodes with respect to a site of the previous orthopedic surgery, thereby increasing a likelihood of efficacious placement of the plurality of electrodes.

In some embodiments, the electrode placement aid comprises at least one of the following: a marking instrument; a template; a measuring device; an x-ray marker; and an imaging device. In certain embodiments, the electrode placement aid comprises at least two of the following: a marking instrument; a template; a measuring device; an x-ray marker; and an imaging device. In certain of these embodiments, the electrode placement aid comprises at least three of the following: a marking instrument; a template; a measuring device; an x-ray marker; and an imaging device.

In some embodiments, the control unit further comprises at least one sensor adapted to provide sensor feedback indicative of a patient parameter derived from the patient.

The invention and its particular features and advantages will become more apparent from the following detailed description considered with reference to the accompanying drawings.

DETAILED DESCRIPTION OF THE INVENTION

Figure 1:
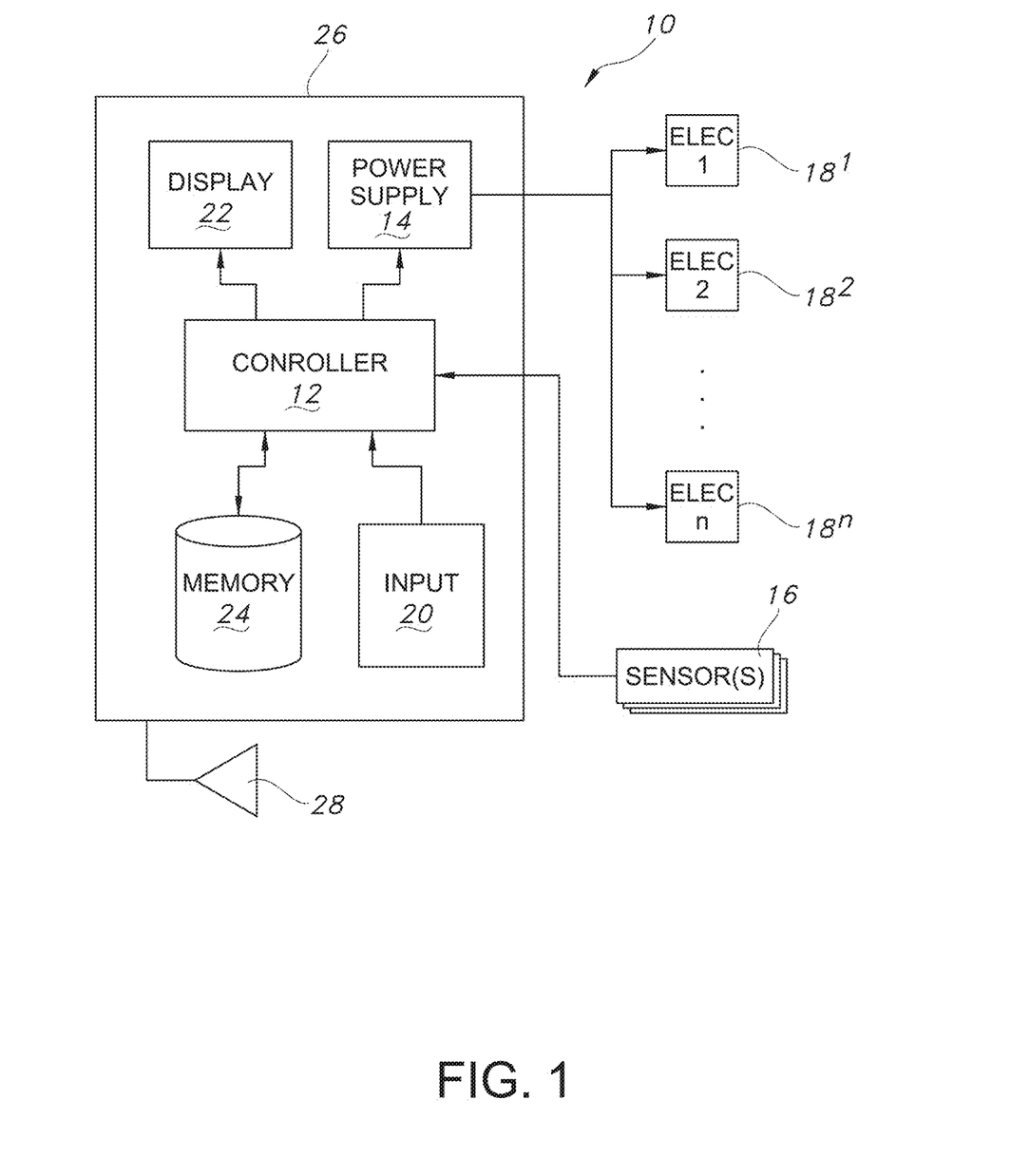
FIG. 1 is a block diagram schematically illustrating a basic device employing interferential current (IFC) therapy together with targeting capabilities to ensure that the stimulating currents are directed to the appropriate areas of the body to achieve the desired results, according to an exemplary embodiment of the present invention.

Referring first to FIG. 1, shown is a system (10) employing the use of an electrical stimulator, such as an Interferential Current (IFC) device, or other type of deep penetration electrical stimulation that is non-invasive and external (i.e., transcutaneous), that may be used in conjunction with the inventive system and method for treatment following orthopedic surgeries. The system (10) includes a controller (12) and a stimulation power supply (14) in communication with the controller (12).

The system (10) also includes a plurality of electrodes ($18^1$, $18^2$ ... $18^n$) in electrical communication with the stimulation power supply (14). The plurality of electrodes ($18^1$, $18^2$ ... $18^n$), the location of which are described further below, are arranged to supply electrical impulses that cause activation of sympathetic and/or parasympathetic nerves when supplied power by the stimulation power supply.

As used herein, the terms "electrode" and "electrodes" encompass electrical coils, electrical plates, electrical conductors, conductive fabrics and gels, and any other conductive materials and devices. Exemplary electrodes that have been found to provide suitable results in connection with the present invention are those distributed by Keystone Rehab Products, LLC of Kingston, Pa. under the QUATRODE™ brand, which conveniently incorporate four separate electrodes (the relevance of which is discussed below) into a single patch.

The controller (12) causes the stimulation power supply (14) to supply power to the plurality of electrodes ($18^1$, $18^2$ ... $18^n$) in response to a command from the controller (12) pursuant to manual user input and/or a program stored thereon. As is explained in more detail below, the power supplied to the plurality of electrodes ($18^1$, $18^2$ ... $18^n$) is such that transcutaneous electrical impulses are created in order to cause sympathetic and/or parasympathetic nerve activation.

The system (10) also includes an input mechanism (20), such as a graphical user interface, microphone for receiving voice commands, keyboard, joystick, or the like, which allows the user to enter control parameters and the like. As examples, input mechanism (20) may include a button or other type of controller to turn the device on or off manually, to trigger activation of sympathetic and/or parasympathetic nerves and/or to allow the user to vary the intensity of the treatments.

In some embodiments, the system may optionally include a sensor (16) providing sensor feedback to the controller (12), and the controller (12) may cause the stimulation power supply (14) to supply power to the plurality of electrodes ($18^1$, $18^2$ ... $18^n$) based, at least in part, on the sensor feedback received from the sensor (16). For instance, the sensor feedback may be indicative of a level of edema present in surgical area, which information may be helpful in tracking progress of past and/or current treatments and/or in helping to define the parameters of current and/or future treatments, such as for example, by varying an intensity of the treatments.

In some embodiments, the system (10) also includes a display (22) to provide visual and/or auditory output to a user of the system (10). The display (22) may also present the user with other helpful information, such as previously loaded data for the patient, or current edema levels and previously recorded edema levels, prior to the supply of power to the electrodes ($18^1$, $18^2$ ... $18^n$), such that a comparison can be made to determine whether the electrical stimulus is actively affecting the targeted pathway.

The system (10) further includes a memory (24), which allows the system to store various parameters that may be employed by the controller (12), or data recorded prior to and/or during the supply of power to the electrodes ($18^1$, $18^2$ ... $18^n$).

In some embodiments the system further includes the ability to transmit information and data obtained through the Internet or other mechanism to remote or off site locations for evaluation by the treating physician, and monitoring of data garnered during or after the treatment, or for incorporation into EMRs, or for telehealth applications.

The controller (12), stimulation power supply (14), input mechanism (20), display (22), memory (24) and an optional antenna (28) for wireless communication may be (but are not necessarily) contained in a housing (26), as should be apparent to those skilled in the art. Various types of connectors may be provided on the housing to allow for connection of the electrodes ($18^1$, $18^2$ ... $18^n$), the sensor (16), or various other devices (e.g., mobile phones, tablets, smart watches, etc.), as should also be apparent to those skilled in the art. This connection may be wired (which requires grounding in a manner similar to that of an electrocoagulation device), or wireless, as further described below.

As will be explained in greater detail below with respect to the exemplary treatment system and method following shoulder surgery, specific targeting for the IFC impulses is important in the context of the present invention so as to avoid the potential for harm to the patient (as has been known to happen, for example, if the electrodes are placed too close to a metal implant), as well as to increase the efficacy of the treatment. Moreover, since the inventive system and method is intended to be employable by the healthcare team (inpatient or outpatient), as well as by the patient himself/herself after being discharged from the hospital or medical facility where the surgery is performed, an electrode placement aid is provided to the patient, for example, as part of an overall kit provided to the patient (as discussed in more detail below).

Although the use of various types of deep penetration electrical stimulation that are non-invasive and external (i.e. transcutaneous) is contemplated, the presently discussed exemplary embodiment employs interferential current (IFC) technology.

In general, IFC therapy utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current were at 4000 Hz and the other current at 3900 Hz, the resultant beat frequency would be at 100 Hz.

Thus, the basic principle of IFC therapy is to utilize the strong physiological effects of the low frequency electrical stimulation of muscle and nerve tissues at sufficient depth, without the associated painful and somewhat unpleasant side effects of such stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current.

In other words, the lower the stimulation frequency, the greater the resistance to the passage of the current, so more discomfort is experienced. The skin impedance at 50 Hz is approximately 3200 ohms, whilst at 4000 Hz, it is reduced to approximately 40 ohms. The result of applying this latter frequency is that it will pass more easily through the skin and any other tissues before hitting the target tissue or organ with a therapeutic beat frequency resulting in the desired physiologic response from the target organ or tissue, requiring less electrical energy input to the deeper tissues, giving rise to less discomfort.

Figure 2:
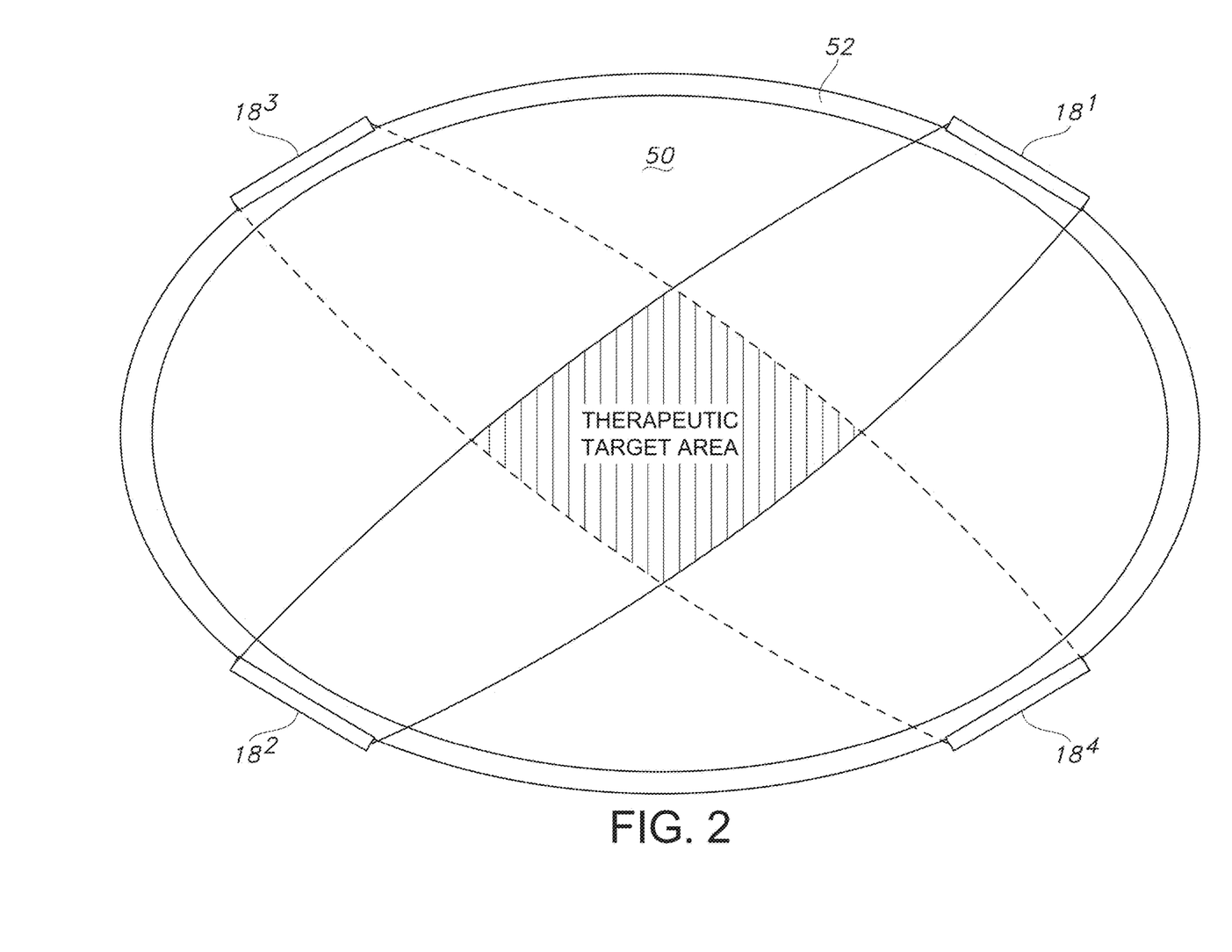
FIG. 2 is schematic view illustrating rudimentary operational characteristics of the device shown in FIG. 1.

Referring now to FIG. 2, an exemplary arrangement of electrodes employing IFC therapy is shown applied to the epidermis (52) of a patient (50). In this example, a first pair of electrodes (18$^1$, 18$^2$) supplies transcutaneous electrical impulses at a first frequency (represented by solid lines) and a second pair of electrodes (18$^3$, 18$^4$) supplies transcutaneous electrical impulses at a second frequency (represented by dashed lines) different than the first frequency. The transcutaneous electrical impulses provided at the first and second frequencies giving rise to a beat impulse in a Therapeutic Target Area (located at the position shown in FIG. 2 where the area defined by solid lines and the area defined by dashed lines overlap) having an interference frequency. The beat impulse results in activation of the sympathetic and/or parasympathetic nerves.

The beat impulse is controlled depending on the type of nerve/tissue/organ to be stimulated, as well as, optionally, on real-time feedback of the elicited response. For example, it has been found that beat impulses having a frequency in the range of from 1-5 Hz may provide desirable stimulation properties for sympathetic nerves, beat impulses having a frequency in the range of from 10-150 Hz may provide desirable stimulation properties for parasympathetic nerves, beat impulses having a frequency in the range of from 10-50 Hz may provide desirable stimulation properties for motor nerves, beat impulses having a frequency in the range of from 90-100 Hz may provide desirable stimulation properties for sensory nerves, beat impulses having a frequency in the range of from 90-150 Hz may provide desirable stimulation properties for nociceptive fibers, and beat impulses having a frequency in the range of from 1-10 Hz may provide desirable stimulation properties for smooth muscle. As will be recognized, other types of nerves/tissues/organs may respond to other beat impulse frequencies.

As has been recognized, nerves will sometimes acclimate to a constant signal. Accordingly, in some embodiments, the electrodes vary the beat frequency, either automatically or upon user input from a medical practitioner, to produce a frequency "sweep" that avoids this problem.

Figure 3:
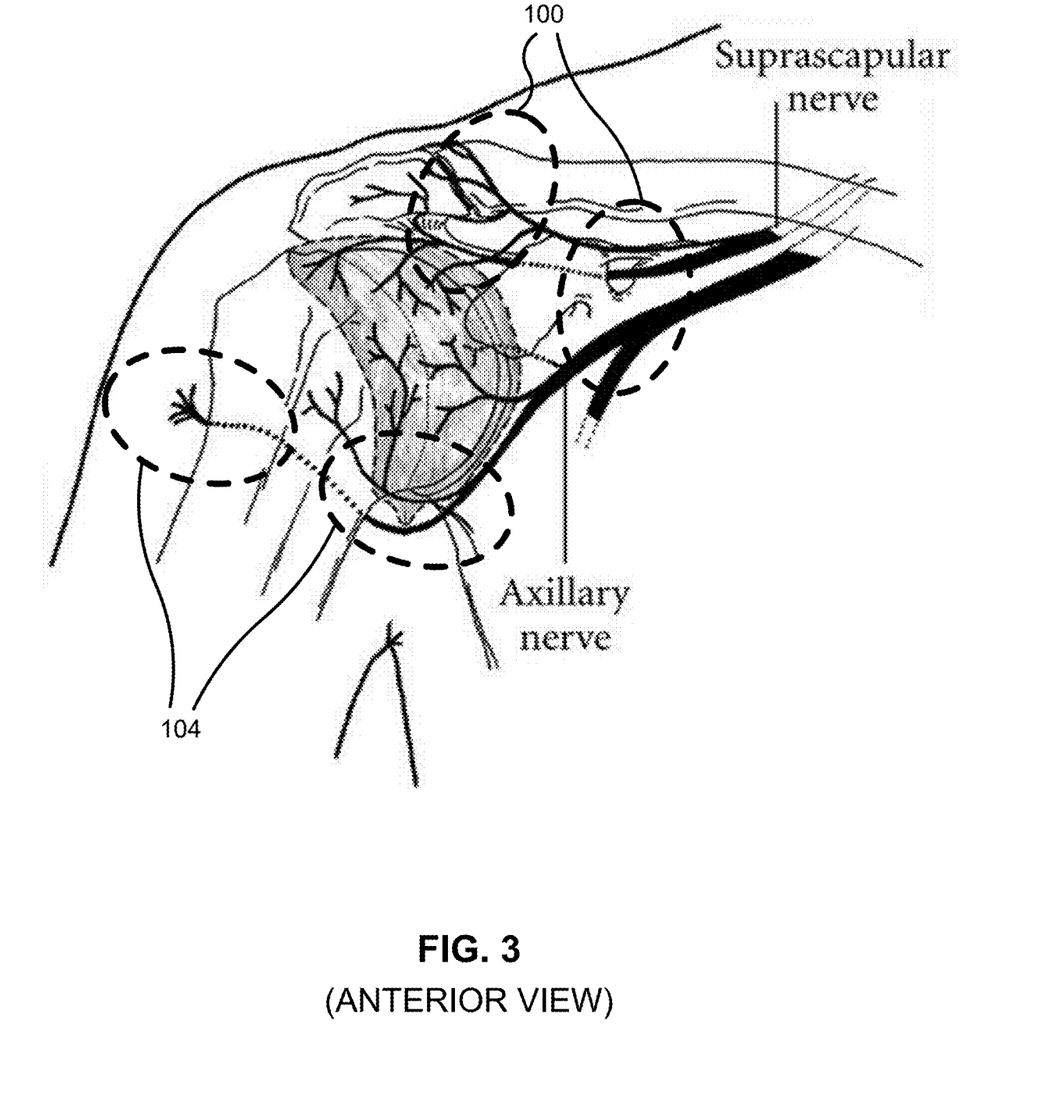
FIGS. 3 and 4 are schematic views illustrating a basic exemplary option for the placement on a patient of the electrodes of the device shown in FIG. 1, particularly for treatment following shoulder surgery.
Figure 4:
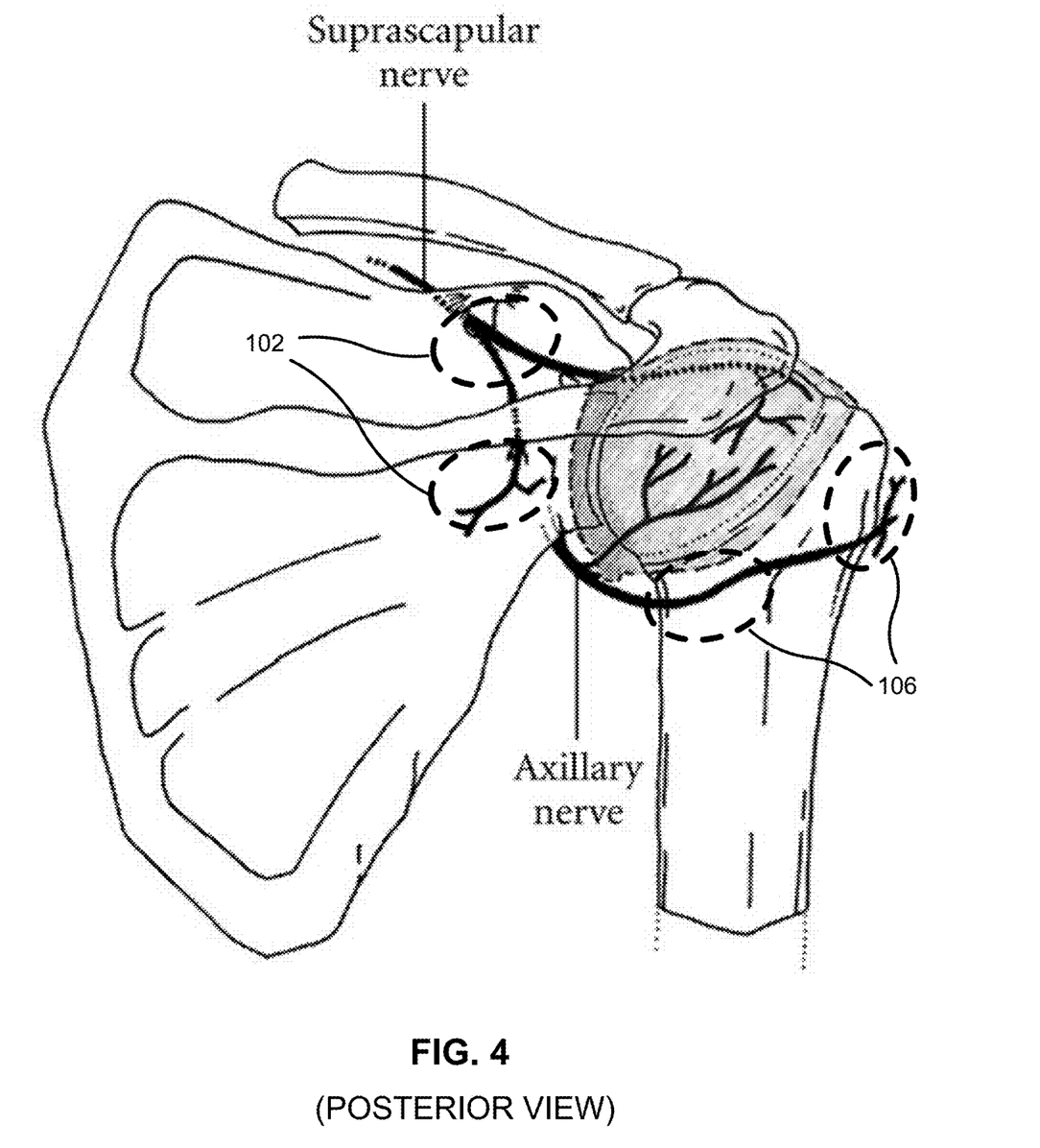

Referring now to FIGS. 3 and 4, an exemplary system and method employing the use an Interferential Current (IFC) device is shown, specifically configured for pain management, increasing range of motion and/or reducing edema following orthopedic shoulder surgery. It should be understood that the term "orthopedic shoulder surgery" is used herein to broadly refer to any of various surgeries performed on the shoulder of a patient, including shoulder arthroscopies, as well as partial and full shoulder arthroplasties, among others, and it is intended that the exemplary embodiment of the present invention shown in FIGS. 3 and 4 can be used following any of such surgeries.

As can be seen, the exemplary embodiment shown in FIGS. 3 and 4 employs two sets of electrodes, a first set stimulating the suprascapular nerve of the patient and a second set stimulating at least one of the axillary nerve and the supraclavicular nerve of the patient.

More particularly, the first, suprascapular nerve stimulating, set of electrodes comprises one pair of electrodes (100) disposed on an anterior of the patient (as schematically shown in FIG. 3) to block deltoid/trapezius and clavicle pain and also axillary, supraclavicular and suprascapular nerves, and another pair of electrodes (102) disposed on a posterior of the patient (as schematically shown in FIG. 4) in an area of the scapula and scapular notch to block the suprascapular nerve. Similarly, the second, axillary/supraclavicular nerve stimulating, set of electrodes comprises one pair of electrodes (104) disposed on an anterior of the patient (as schematically shown in FIG. 3) on the upper arm to block axillary and/or supraclavicular nerve pain fibers and another pair of electrodes (106) disposed on a posterior of the patient (as schematically shown in FIG. 4) on the upper arm to block the axillary nerve and/or the supraclavicular nerve.

Various configurations for the electrodes are possible. For example, each individual electrode, or each pair of electrodes (100, 102, 104, 106) can be disposed on a separate pad. However, it may be desirable for each pad to carry four electrodes (i.e., two pairs of electrodes) in order to facilitate electrode placement. For example, the anterior suprascapular nerve stimulating pair of electrodes (100) and the anterior axillary/supraclavicular nerve stimulating pair of electrodes (104) may all be carried on a single pad, configured to be disposed on the anterior of the patient (see FIG. 3). Similarly, the posterior suprascapular nerve stimulating pair of electrodes (102) and the posterior axillary/supraclavicular nerve stimulating pair of electrodes (106) may all be carried on another single pad, configured to be disposed on the posterior of the patient (see FIG. 4).

The precise types and sizes of the electrodes and/or the pads carrying the electrodes may vary based on, for example, the size of the patient. However, it has been found that the "large" (i.e., 6.75 inches; 17 cm) QUATRODE™ brand electrode pads distributed by Keystone Rehab Products, LLC of Kingston, Pa. may provide desirable results for at least some patients, while it has been found that the "medium" (i.e., 4.50 inches; 11 cm) QUATRODE™ brand electrode pads distributed by Keystone Rehab Products, LLC of Kingston, Pa. may provide desirable results for other patients.

Multiple other options for electrode placement that will be effective are derived from the relevant anatomy used by anesthesia to administer regional block anesthesia such as is currently used for shoulder surgery pain control (e.g., axillary, supraclavicular and/or suprascapular nerve blocks). This would allow one to prep over the marking of the injection site for surgery, and for the quatrode to be centered over the mark, with the center of the quatrode being on the mark. In this case, the overall system and kit of the present invention would essentially be functioning as an ongoing intermittent regional block that is electrical in nature, as opposed to when the medication in the regional block itself wears off after anywhere from 6 to 24 hours.

The exemplary positioning shown in FIGS. 3 and 4 also takes into account areas to be avoided, in addition to electrodes being placed too close to an implant (and then causing skin aggravation by scattering of the currents so that they may become too strong in an area and cause burns or other complications).

As mentioned above, since the inventive system and method is intended to be employable by the healthcare team (inpatient or outpatient), as well as by the patient himself/ herself after being discharged from the hospital or medical facility where the surgery is performed, an electrode placement aid is provided to the patient, for example, as part of an overall kit provided to the patient.

Figure 5:
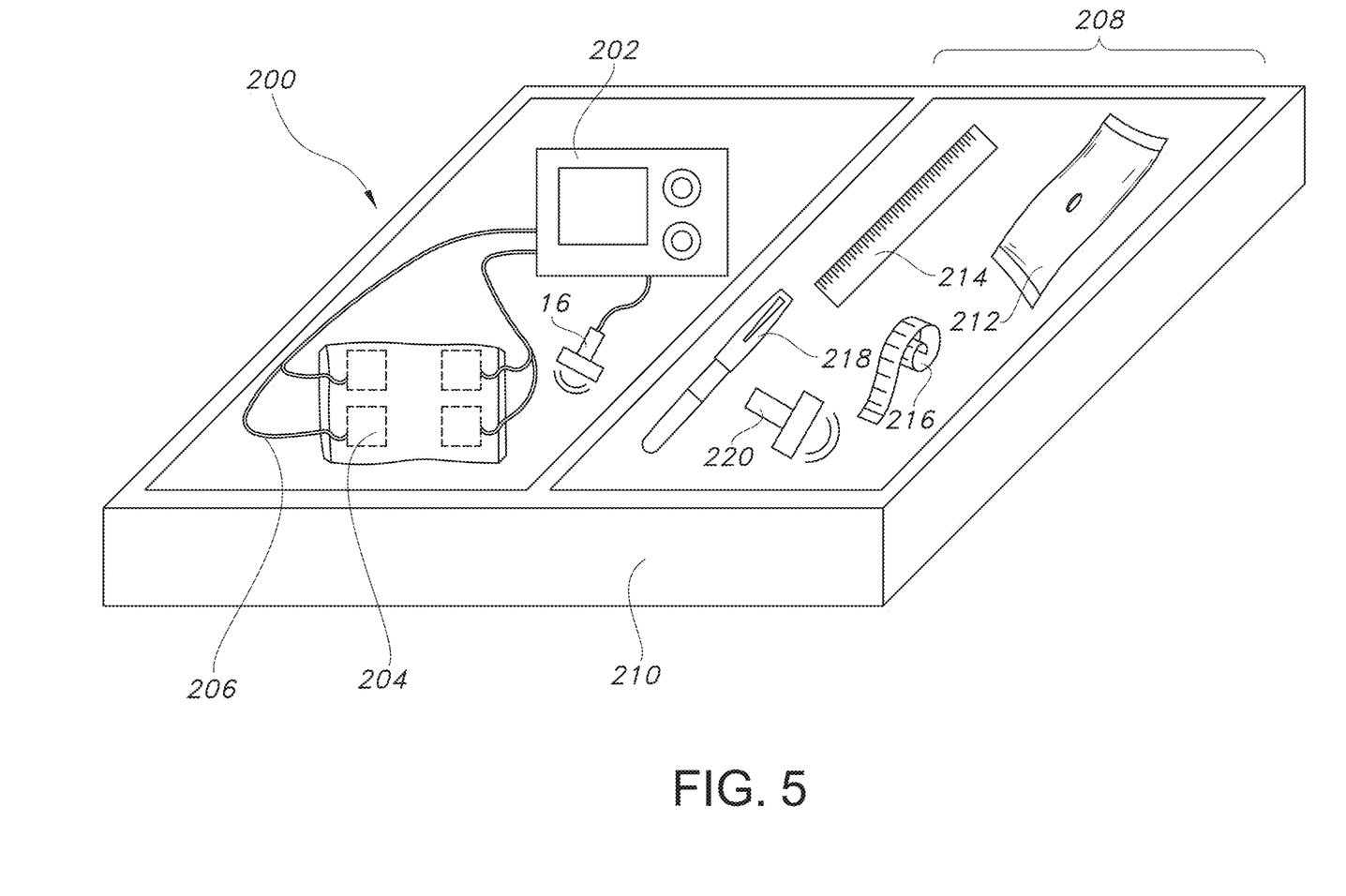
FIG. 5 is a schematic view of an exemplary kit employing the use of an electrical stimulator, such as an Interferential Current (IFC) device, or other type of deep penetration electrical stimulation that is non-invasive and external (i.e., transcutaneous), for treatment following orthopedic surgeries.

Such an exemplary kit (200), an example of which is shown in FIG. 5, may include one or multiple control units (202), which may include, for example, some or all of the components disposed within the housing (26) of FIG. 1. For example, the control unit (202) may include the controller (12), the power supply (14), the input (20), the memory (24) and the wireless antenna (28), if provided. Additionally, the kit (200) includes a plurality of electrodes (204), which may or may not be disposed on common pads, as described in more detail above, as well as any necessary wire leads (206) for connecting the electrodes to the control unit (202). The kit (200) may also include one or more sensors (16) providing sensor feedback to the control unit (202), as described above. Additionally, of critical importance given the nature of the kit (200) for home use, one or more electrode placement aids (208) are also provided in the kit (200).

In order to facilitate distribution and transportation of the kit (200), as well as to ensure that all necessary components are included, the kit is provided in a container (210), such as a box, a bag, a tray or the like. A plurality of different kits may be produced having different components, depending on such factors as the type of surgery having been performed, the size of the patient, etc. Moreover, the control unit/IFC generating device (202) contained in the kit (200) is preferably already programmed for efficacy and safety of the power supply for the electrodes and the fields that result, either by the manufacturer, or by the health care team prior to the patient's surgery. As such, little or no input by the patient or ancillary members of the treatment team is necessary during inpatient treatment or once in the home environment, thereby reducing the chances of injury caused by accidental misuse.

Figure 6:
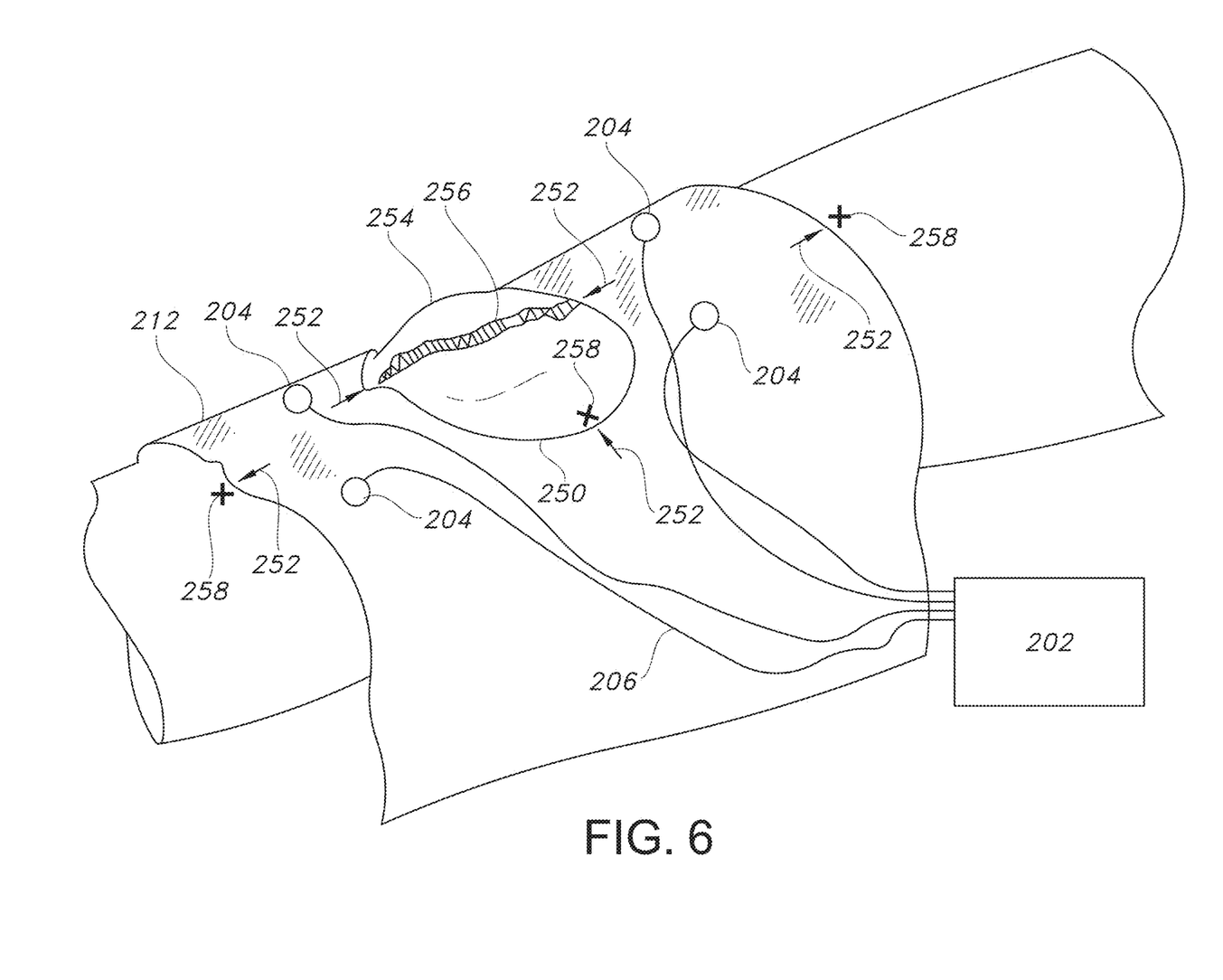
FIG. 6 is a schematic view showing in more detail an exemplary template that may be employed in connection with the inventive kit illustrated in FIG. 5.

The electrode placement aid (208) may take any of various forms. For example, referring specifically to FIG. 6, the electrode placement aid (208) may take the form of a template, drape or the like that may include one or more openings (250) and/or markings (252) showing the relative intended placement of the electrodes with respect to anatomical structure (254), an incision (256) and/or markings (258) made on the patient. Such a template, drape or the like is collectively referred to herein as a template (212). The template (212) may incorporate the electrodes (204) as part of its structure and/or be constructed so as to be applied directly to the patient as part of the immediate post-operative dressing (as seen, for example, with dressing and drain systems, including the PREVENA™ incision management system). While the exemplary template shown in FIG. 6 is for the knee of a patient, the template can easily be adapted for shoulder surgery and/or surgery on some other part of the body.

As another example of the electrode placement aid (208), a measuring device (214) such as a ruler or tape measure may be provided or incorporated into, or directly attached to the quatrode, along with instructions and/or diagrams or the like detailing measurements and relative positioning of the electrodes with respect to anatomical structure, incisions, markings (e.g., drawn on the patient with permanent marker), etc.

Various x-ray markers (216) may be incorporated into the template or quatrode assembly to be used as targets for positioning or to verify position after deployment, but before turning on the device. Regarding x-ray, these may be in the nature of radiology tape with metal beads, or radiology tape with a central strip of radiopaque marker or other radiology devices which are radiopaque, but are not metallic in nature. Such markers or measuring devices can be used based on established special relationships to remove and replace electrodes over time so that the skin is not irritated by leaving the electrodes and the adhering backing of the electrodes for too long in one place.

A marking device (218), such as a permanent ink marking pen may be part of the kit to be used to provide an outline or a memory graphic or lines to guide the placement of the quatrode or electrode to be reattached in terms of skin care, with the electrode being placed within the outline.

The electrode placement aid (208) may also take the form of an imaging device (220), such as a sensor provided in addition or instead of the aforementioned feedback sensor (16), which is useable by the patient in the home environment. Examples of such imaging devices (220) are becoming more common, and may for example, take the form of a sensor that may be plugged into, for example, a mobile phone or other mobile device. One specific example of such a device, currently being distributed by Butterfly Networks, Inc. under the name Butterfly iQ, is an ultrasound imaging device that is a direct connect to the mobile phone. This system, which may be used as part of a targeting combination with an IFC device, allows the IFC device to be positioned when the metal of the replacement is shown on the ultrasound, and may also be used to correlate device electrode placement with the neurovascular bundles being injected by the anesthesiologist for the nerve blocks.

Moreover, when the electrode placement aid (208) is a mobile device app, additional features for targeting and transferring data may be employed. For example, a mobile phone may be used to take a photograph of the freshly closed post op wound (for size and length measurements). The app then processes this photo data and returns a picture for the surgeon (and team) that describes the landmarks previously mentioned and shows where the electrodes are to be placed, as well as their distance from the wound and other structures. This information may then be stored in the app and subsequently transmitted to the patient's individual electrical medical record (EMR) for use by other members of the team, such as the physical therapist, to replace or reposition the electrodes for subsequent treatments if the original positioning is lost or altered (i.e., to provide a "photographic/picture" targeting mechanism). This then helps to cover all the variations of incisions that are currently being used to be specific for that particular patient as to how the size of the wound gets incorporated into the determination as to how close the electrodes are placed to the fresh wound post op.

The app (or any of the targeting devices already described) preferably also has an algorithm incorporated that includes the size of any prosthesis into the calculation of the size, location and positioning of the electrodes associated with the targeting mechanism. In this regard, joint replacements are manufactured in standard sizes by a multitude of orthopedic implant providers that more or less accommodate the variation in the size of each patient's bone. The decision of type and size of implants available for use by the surgeon thus results in innumerable options. For example, one well-known implant manufacturer makes multiple standardized implants (e.g., male-small, medium, large/female-small, medium, large) for which the sizes relate to each of the femoral and tibial replacements, thus resulting in a minimum of nine different variations of size of the replacement used for each sex (e.g., large femoral component may match a medium tibial component).

Although the exemplary use for the invention has been described herein for orthopedic shoulder surgery, it will be ascertainable to those of skill in the art that such use and safe application of the invention's systems and methods can be applied to, and modified to be employed in, many other types of orthopedic surgery.

Placement of the electrodes may be varied depending on the particular type of surgery performed. For example, while the exemplary electrode placement locations described in detail above in connection with orthopedic shoulder surgery may also be appropriate for other types of shoulder surgeries, other placement locations may instead be used as appropriate. For surgeries on other anatomical structures, various other electrode placements may be employed, such as, for example, focusing on nerve block sites known to be used in connection with anesthetizing those anatomical structures upon which surgery has been performed.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An interferential current therapy kit for treatment of a patient following an orthopedic shoulder surgery, said kit comprising, within a container for facilitating the distribution and transport of said kit, the following:
a first plurality of electrodes configured to be disposed on an epidermis of the patient and arranged to supply transcutaneous electrical impulses to a suprascapular nerve of the patient when supplied with power, wherein said first plurality of electrodes comprises at least two electrodes adapted to supply transcutaneous electrical impulses at two different frequencies, the transcutaneous electrical impulses provided at two different frequencies adapted to give rise to at least one first beat impulse having an interference frequency;
a second plurality of electrodes configured to be disposed on the epidermis of the patient and arranged to supply transcutaneous electrical impulses to at least one of an axillary nerve and a supraclavicular nerve of the patient when supplied with power, wherein said second plurality of electrodes comprises at least two electrodes adapted to supply transcutaneous electrical impulses at two different frequencies, the transcutaneous electrical impulses provided at two different frequencies adapted to give rise to at least one second beat impulse having an interference frequency;
an interferential current therapy control unit comprising a stimulation power supply in electrical communication with said first plurality of electrodes and said second plurality of electrodes, said interferential current therapy control unit configured to supply interferential current electrical impulses so as to give rise to the at least one first beat impulse acting on the suprascapular nerve of the patient and so as to give rise to the at least one second beat impulse acting on at least one of the axillary nerve and the supraclavicular nerve of the patient; and
an electrode placement aid adapted to assist the patient with the relative placement of said first and second pluralities of electrodes with respect to anatomical structure such that said interferential current therapy control unit generates the at least one first beat impulse on the suprascapular nerve of the patient and the second beat impulse on at least one of the axillary nerve and the supraclavicular nerve of the patient.

2. The interferential current therapy kit of claim 1, wherein said electrode placement aid comprises a marking instrument.

3. The interferential current therapy kit of claim 2, wherein the marking instrument comprises an ink marker.

4. The interferential current therapy kit of claim 1, wherein said electrode placement aid comprises a template.

5. The interferential current therapy kit of claim 4 wherein the template comprises a drape that includes at least one of openings and markings showing a relative intended placement of said plurality of electrodes with respect to anatomical structure.

6. The interferential current therapy kit of claim 1, wherein said electrode placement aid comprises a measuring device.

7. The interferential current therapy kit of claim 6, wherein the measuring device comprises at least one of a ruler and a tape measure.

8. The interferential current therapy kit of claim 1, wherein said electrode placement aid comprises an x-ray marker.

9. The interferential current therapy kit of claim 8, wherein the x-ray marker comprises at least one of the following: radiology tape with metal beads, radiology tape with a central strip of radiopaque marker and other radiology devices which are radiopaque, but are not metallic in nature.

10. The interferential current therapy kit of claim 1, wherein said electrode placement aid comprises an imaging device adapted to assist with electrode placement.

11. The interferential current therapy kit of claim 10, wherein the imaging device is adapted to interface with a mobile phone or tablet.

12. The interferential current therapy kit of claim 1, wherein said electrode placement aid is adapted to interface with markings created on a body of the patient.

13. The interferential current therapy kit of claim 1, wherein said control unit further comprises at least one sensor adapted to provide sensor feedback indicative of a patient parameter derived from the patient.

14. The interferential current therapy kit of claim 1, further comprising a plurality of wire leads adapted to connect said control unit with said plurality of electrodes.

15. The interferential current therapy kit of claim 1, wherein said first plurality of electrodes comprises a first pair of electrodes configured to be disposed on an anterior of the patient and arranged to supply transcutaneous electrical impulses to the suprascapular nerve of the patient when supplied with power and a second pair of electrodes configured to be disposed on a posterior of the patient and arranged to supply transcutaneous electrical impulses to the suprascapular nerve of the patient when supplied with power.

16. The interferential current therapy kit of claim 1, wherein said second plurality of electrodes comprises a first pair of electrodes configured to be disposed on an anterior of the patient and arranged to supply transcutaneous electrical impulses to at least one of the axillary nerve and the supraclavicular nerve of the patient when supplied with power and a second pair of electrodes configured to be disposed on a posterior of the patient and arranged to supply transcutaneous electrical impulses to at least one of the axillary nerve and the supraclavicular nerve of the patient when supplied with power.

17. An interferential current therapy kit for treatment of a patient following an orthopedic shoulder surgery, said kit comprising:

a first plurality of electrodes configured to be disposed on an epidermis of the patient and arranged to supply transcutaneous electrical impulses to a suprascapular nerve of the patient when supplied with power, wherein said first plurality of electrodes comprises at least two electrodes adapted to supply transcutaneous electrical impulses at two different frequencies, the transcutaneous electrical impulses provided at two different frequencies adapted to give rise to at least one first beat impulse having an interference frequency;

said first plurality of electrodes comprising a first pair of electrodes configured to be disposed on an anterior of the patient and arranged to supply transcutaneous electrical impulses to the suprascapular nerve of the patient when supplied with power and a second pair of electrodes configured to be disposed on a posterior of the patient and arranged to supply transcutaneous electrical impulses to the suprascapular nerve of the patient when supplied with power;

a second plurality of electrodes configured to be disposed on the epidermis of the patient and arranged to supply transcutaneous electrical impulses to at least one of an axillary nerve and a supraclavicular nerve of the patient when supplied with power, wherein said second plurality of electrodes comprises at least two electrodes adapted to supply transcutaneous electrical impulses at two different frequencies, the transcutaneous electrical impulses provided at two different frequencies adapted to give rise to at least one second beat impulse having an interference frequency;

said second plurality of electrodes comprises a third pair of electrodes configured to be disposed on an anterior of the patient and arranged to supply transcutaneous electrical impulses to at least one of the axillary nerve and the supraclavicular nerve of the patient when supplied with power and a fourth pair of electrodes configured to be disposed on a posterior of the patient and arranged to supply transcutaneous electrical impulses to at least one of the axillary nerve and the supraclavicular nerve of the patient when supplied with power;

an interferential current therapy control unit comprising a stimulation power supply in electrical communication with said first plurality of electrodes and said second plurality of electrodes, said interferential current therapy control unit configured to supply interferential current electrical impulses so as to give rise to the at least one first beat impulse acting on the suprascapular nerve of the patient and so as to give rise to the at least one second beat impulse acting on at least one of the axillary nerve and the supraclavicular nerve of the patient; and an electrode placement aid adapted to assist the patient with placement of said first and second plurality of electrodes with respect to anatomical structure such that said interferential current therapy control unit generates the at least one first beat impulse on the suprascapular nerve of the patient and the second beat impulse on at least one of the axillary nerve and the supraclavicular nerve of the patient, thereby increasing a likelihood of efficacious placement of said plurality of electrodes.

18. The interferential current therapy kit of claim 17, wherein said electrode placement aid comprises at least one of the following:

a marking instrument;
a template;
a measuring device;
an x-ray marker; and
an imaging device.

19. The interferential current therapy kit of claim 18, wherein said electrode placement aid comprises at least two of the following:

a marking instrument;
a template;
a measuring device;
an x-ray marker; and
an imaging device.

20. The interferential current therapy kit of claim 19, wherein said electrode placement aid comprising at least three of the following:

a marking instrument;
a template;
a measuring device;
an x-ray marker; and
an imaging device.

21. The interferential current therapy kit of claim 17, wherein said control unit further comprises at least one sensor adapted to provide sensor feedback indicative of a patient parameter derived from the patient.

* * * * *